US010020449B2

(12) United States Patent
Oshima et al.

(10) Patent No.: US 10,020,449 B2
(45) Date of Patent: Jul. 10, 2018

(54) COMPOSITION FOR ANODE BUFFER LAYER OF ORGANIC THIN FILM SOLAR CELL AND ORGANIC THIN FILM SOLAR CELL

(71) Applicant: NISSAN CHEMICAL INDUSTRIES, LTD., Tokyo (JP)

(72) Inventors: Juro Oshima, Funabashi (JP); Takuji Yoshimoto, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/102,775

(22) PCT Filed: Dec. 5, 2014

(86) PCT No.: PCT/JP2014/082228
§ 371 (c)(1),
(2) Date: Jun. 8, 2016

(87) PCT Pub. No.: WO2015/087797
PCT Pub. Date: Jun. 18, 2015

(65) Prior Publication Data
US 2016/0315266 A1 Oct. 27, 2016

(30) Foreign Application Priority Data
Dec. 9, 2013 (JP) ................. 2013-254159

(51) Int. Cl.
| H01B 1/12 | (2006.01) |
|---|---|
| H01L 51/00 | (2006.01) |
| C07C 309/43 | (2006.01) |
| C07C 211/54 | (2006.01) |
| C07C 211/55 | (2006.01) |
| C08K 3/04 | (2006.01) |
| C08L 65/00 | (2006.01) |
| H01L 51/42 | (2006.01) |
| H01L 51/44 | (2006.01) |

(52) U.S. Cl.
CPC ........ *H01L 51/0036* (2013.01); *C07C 211/54* (2013.01); *C07C 211/55* (2013.01); *C07C 309/43* (2013.01); *C08K 3/045* (2017.05); *H01B 1/12* (2013.01); *H01L 51/0047* (2013.01); *H01L 51/0052* (2013.01); *H01L 51/0058* (2013.01); *H01L 51/0059* (2013.01); *H01L 51/0094* (2013.01); *C08G 2261/146* (2013.01); *C08G 2261/1412* (2013.01); *C08G 2261/1424* (2013.01); *C08G 2261/1428* (2013.01); *C08G 2261/3246* (2013.01); *C08G 2261/344* (2013.01); *C08G 2261/91* (2013.01); *C08L 65/00* (2013.01); *H01L 51/0043* (2013.01); *H01L 51/0046* (2013.01); *H01L 51/424* (2013.01); *H01L 51/441* (2013.01); *Y02E 10/549* (2013.01)

(58) Field of Classification Search
CPC ............. H01L 51/5052; H01L 51/5056; H01L 51/5088; H01L 51/5092; H01L 51/0036; H01L 51/0043; H01L 51/0046; H01L 51/0047; H01L 51/0052; H01L 51/0058; H01L 51/0059; H01L 51/0094; H01L 51/424; H01L 51/441; Y02E 10/549; H01B 1/00; H01B 1/12; C08K 3/045; C08L 65/00; C07C 211/54; C07C 211/55; C07C 309/43; C08G 2261/1412; C08G 2261/1424; C08G 2261/1428; C08G 2261/146; C08G 2261/3246; C08G 2261/344; C08G 2261/91
See application file for complete search history.

(56) References Cited

U.S. PATENT DOCUMENTS

| 6,416,818 | B1 * | 7/2002 | Aikens | ............... | B82Y 30/00 |
|---|---|---|---|---|---|
| | | | | | 427/383.1 |
| 9,487,618 | B2 * | 11/2016 | Hayer | ............... | C08G 61/02 |
| 2002/0182440 | A1 * | 12/2002 | Seki | ............... | H01L 51/0035 |
| | | | | | 428/690 |
| 2007/0181874 | A1 * | 8/2007 | Prakash | ............... | B82Y 10/00 |
| | | | | | 257/40 |
| 2008/0061685 | A1 * | 3/2008 | Chesterfield | ........ | H01L 51/0035 |
| | | | | | 313/504 |
| 2009/0270585 | A1 | 10/2009 | Yoshimoto et al. | | |

(Continued)

FOREIGN PATENT DOCUMENTS

| CN | 102227830 | 10/2011 |
|---|---|---|
| EP | 2062871 A1 | 5/2009 |

(Continued)

OTHER PUBLICATIONS

International Search Report issued in PCT/JP2014/082228 dated Jan. 20, 2015.

(Continued)

*Primary Examiner* — Mark Kopec
*Assistant Examiner* — Jaison P Thomas
(74) *Attorney, Agent, or Firm* — Birch, Stewart, Kolasch & Birch, LLP

(57) ABSTRACT

Provided is a composition comprising: a charge-transporting substance that comprises N,N'-diphenylbenzidine; an electron-accepting dopant substance; and an organic solvent. This composition is suitable, for example, as a composition for the anode buffer layer of an organic thin film solar cell, said composition being used to produce a thin film that is suitable for use as an anode buffer layer that makes it possible to achieve an organic thin film solar cell having a high photoelectric conversion efficiency.

10 Claims, No Drawings

(56) References Cited

U.S. PATENT DOCUMENTS

| | | | |
|---|---|---|---|
| 2010/0045174 A1* | 2/2010 | Okabe | C08G 65/18 |
| | | | 313/504 |
| 2010/0147386 A1* | 6/2010 | Benson-smith | H01L 51/002 |
| | | | 136/263 |
| 2010/0230639 A1 | 9/2010 | Yamada et al. | |
| 2010/0301277 A1 | 12/2010 | Hartmann et al. | |
| 2011/0195355 A1 | 8/2011 | Nakaie et al. | |
| 2014/0227815 A1 | 8/2014 | Nakaie et al. | |
| 2015/0090977 A1* | 4/2015 | Imai | H01L 51/0013 |
| | | | 257/40 |
| 2016/0005975 A1* | 1/2016 | Nakaie | H01L 51/0059 |
| | | | 438/46 |

FOREIGN PATENT DOCUMENTS

| | | |
|---|---|---|
| EP | 2143708 A1 | 1/2010 |
| JP | 2010-530845 A | 9/2010 |
| WO | WO 2013/042623 A1 | 3/2013 |

OTHER PUBLICATIONS

Li et al., "Polymer solar cells", Nature Photonics, vol. 6, pp. 153-161, Mar. 2012.

O'Regan et al., "A low-cost, high-efficiency solar cell based on dye-sensitized colloidal TiO2 films", Nature, vol. 353, pp. 737-740, Oct. 24, 1991.

Sun et al., Chemically Doped and Cross-linked Hole-Transporting Materials as an Efficient Anode Buffer Layer for Polymer Solar Cells, Chemistry of Materials, vol. 23, Issue 22, pp. 5006-5015, Oct. 25, 2011.

Tang, "Two-layer organic photovoltaic cell", Appl. Phys. Lett. vol. 48, pp. 183-185, Jan. 13, 1986.

Written Opinion of the International Searching Authority issued in PCT/JP2014/082228 dated Jan. 20, 2015.

Extended European Search Report for European Application No. 14870013.1, dated Jul. 10, 2017.

Chinese Office Action for Application No. 201480074096.4, dated Jan. 10, 2018.

* cited by examiner

COMPOSITION FOR ANODE BUFFER LAYER OF ORGANIC THIN FILM SOLAR CELL AND ORGANIC THIN FILM SOLAR CELL

TECHNICAL FIELD

The present invention relates to a composition for an anode buffer layer of an organic thin film solar cell, and an organic thin film solar cell.

BACKGROUND ART

Organic thin film solar cells are solar cell elements using organic matter for an active layer and as a charge-transporting substance, among which the dye-sensitized solar cell developed by M. Gratzel and the organic thin film solar cell developed by C. W. Tang are well known (Non-patent Documents 1 and 2).

Both types of solar cells have different characteristic properties from those of the inorganic solar cells which are the main stream at present, in such points that they are light in weight, are thin films, can be made to be flexible, and can be produced on a roll-to-roll basis, so that they are expected to form a new market.

Among others, the organic thin film solar cells (organic photovoltaics; hereinafter abbreviated to OPV) have been drawing great attention, since they are characterized in that they are at least free of electrolytes and free of heavy metal compounds, and since a photoelectric conversion efficiency (hereinafter abbreviated to PCE) of 10.6% has recently been reported by a group of UCLA et al. (Non-patent Document 3).

In recent years, utilization of renewable energy has been advocated, and developments thereof have been being accelerated. In regard of the OPV, investigations have been under way for putting devices of energy harvesting and the like into practical use in their early stages. Besides, the following further wider ranges of use of the OPV devices are expected.

However, PEDOT/PSS often used as an anode buffer layer in the OPV is prepared as an aqueous dispersion, and it is very difficult to remove water completely or to inhibit reabsorption of water; therefore, there is a problem that water is liable to accelerate deterioration of the OPV element. In addition, since the PEDOT/PSS aqueous dispersion liable to show aggregation of solids, there are problems that defects are liable to be generated in the coating film, that the coating apparatus is susceptible to clogging or corrosion, etc.; thus, there have been problems yet to be solved, also in the mass production process.

PRIOR ART DOCUMENTS

Non-Patent Documents

Non-Patent Document 1: Nature, vol. 353, 737-740 (1991)
Non-Patent Document 2: Appl. Phys. Lett., Vol. 48, 183-185 (1986)
Non-Patent Document 3: Nature Photonics Vol. 6, 153-161 (2012)

SUMMARY OF THE INVENTION

Problems to be Solved by the Invention

The present invention has been made in consideration of the above-mentioned circumstances. Accordingly, it is an object of the present invention to provide a composition that gives a thin film suitable for an anode buffer layer of an organic thin film solar cell.

Means for Solving the Problems

In order to achieve the above object, the present inventors earnestly made investigations. As a result of the investigations, the inventors found out that a composition containing an aryldiamine derivative and an electron-accepting dopant substance is completely dissolved in an organic solvent to form a uniform solution, and that when a thin film obtained from the uniform solution is used as an anode buffer layer of an organic thin film solar cell, it is thereby possible to obtain an organic thin film solar cell having excellent photoelectric conversion characteristics. Based on the findings, the inventors have completed the present invention.

Accordingly, the present invention provides:

1. A composition for an anode buffer layer of an organic thin film solar cell, the composition including: a charge-transporting substance including an aryldiamine derivative represented by the formula (1); an electron-accepting dopant substance; and an organic solvent;

[Chemical Formula 1]

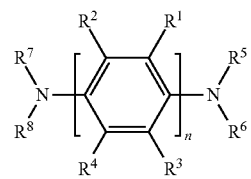

(1)

{In the formula, $R^1$ to $R^4$ each independently represent a hydrogen atom, a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group, $R^5$ to $R^8$ each independently represent a hydrogen atom, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group, a thienyl group (These groups may be substituted with a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group.), or a group represented by the formula (2) (Provided that at least one of $R^5$ to $R^8$ is a hydrogen atom.),

[Chemical Formula 2]

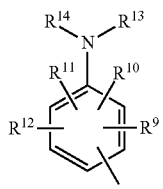

(2)

[In the formula, $R^9$ to $R^{12}$ each independently represent a hydrogen atom, a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group, and $R^{13}$ and $R^{14}$ each independently represent a phenyl group, a naphthyl group, an anthryl group, a pyridyl group, a pyrimidinyl group, a pyridazinyl group, a pyrazinyl group, a furanyl group, a pyrrolyl group, a pyrazolyl group, an imidazolyl group, a thienyl group (These groups may be bonded to each other to form a ring, and may be substituted with a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group.)], and n represents an integer of 2 to 5.}

2. The composition for an anode buffer layer of an organic thin film solar cell according to the above paragraph 1, wherein $R^5$ and $R^7$ are hydrogen atoms, and $R^6$ and $R^8$ are phenyl groups;

3. The composition for an anode buffer layer of an organic thin film solar cell according to the above paragraph 1 or 2, wherein n is 2 or 3;

4. The composition for an anode buffer layer of an organic thin film solar cell according to any one of the above paragraphs 1 to 3, wherein the electron-accepting dopant substance includes an arylsulfonic acid compound;

5. The composition for an anode buffer layer of an organic thin film solar cell according to the above paragraph 4, wherein the arylsulfonic acid compound is represented by the formula (3);

[Chemical Formula 3]

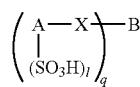

(3)

(In the formula, letter X represents O, letter A represents a naphthalene ring or an anthracene ring, letter B represents a perfluorobiphenyl group having a valence of 2 to 4, letter l represents the number of sulfonic acid groups bonded to A and is an integer satisfying 1≤l≤4, and letter q represents the number of bonds of the letter B and the letter X and is an integer satisfying 2 to 4.)

6. The composition for an anode buffer layer of an organic thin film solar cell according to the above paragraph 5, wherein the letter X represents O, and the letter A represents a naphthalene ring or an anthracene ring;

7. The composition for an anode buffer layer of an organic thin film solar cell according to any one of the above paragraphs 1 to 6, including an organosilane compound;

8. An organic thin film solar cell including: an anode buffer layer produced from the composition for an anode buffer layer of an organic thin film solar cell according to any one of the above paragraphs 1 to 7; and an active layer provided in such a manner as to make contact with the anode buffer layer;

9. The organic thin film solar cell according to the above paragraph 8, wherein the active layer includes a fullerene derivative;

10. The organic thin film solar cell according to the above paragraph 8, wherein the active layer includes a polymer including a thiophene skeleton in a main chain; and 11. The organic thin film solar cell according to the above paragraph 8, wherein the active layer includes a fullerene derivative and a polymer including a thiophene skeleton in a main chain.

Advantageous Effects of the Invention

The composition of the present invention not only can be produced by use of compounds inexpensively available from the market, but also ensures that when a thin film obtained therefrom is used as an anode buffer layer, it is possible to obtain an organic thin film solar cell having an excellent photoelectric conversion efficiency.

EMBODIMENT FOR CARRYING OUT THE INVENTION

The present invention will be described more in detail below.

The composition for an anode buffer layer of an organic thin film solar cell of the present invention includes an aryldiamine derivative of the above formula (1), an electron-accepting dopant substance, and an organic solvent.

$R^1$ to $R^4$ each independently represent a hydrogen atom, a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group.

Here, examples of the halogen atom include fluorine, chlorine, bromine, and iodine atoms.

Specific examples of the C1-C20 alkoxy group include methoxy group, ethoxy group, n-propoxy group, i-propoxy group, c-propoxy group, n-butoxy group, i-butoxy group, s-butoxy group, t-butoxy group, n-pentoxy group, n-hexoxy group, n-heptyloxy group, n-octyloxy group, n-nonyloxy group, n-decyloxy group, n-undecyloxy group, n-dodecyloxy group, n-tridecyloxy group, n-tetradecyloxy group, n-pentadecyloxy group, n-hexadecyloxy group, n-heptadecyloxy group, n-octadecyloxy group, n-nonadecyloxy group, and n-eicosanoyloxy group.

Specific examples of the C1-C20 thioalkoxy (alkylthio) group include methylthio group, ethylthio group, n-propylthio group, isopropylthio group, n-butylthio group, isobutylthio group, s-butylthio group, t-butylthio group, n-pentylthio group, n-hexylthio group, n-heptylthio group, n-octylthio group, n-nonylthio group, n-decylthio group, n-undecylthio group, n-dodecylthio group, n-tridecylthio group, n-tetradecylthio group, n-pentadecylthio group, n-hexadecylthio group, n-heptadecylthio group, n-octadecylthio group, n-nonadecylthio group, and n-eicosanylthio group.

Specific examples of the C1-C20 alkyl group include methyl group, ethyl group, n-propyl group, isopropyl group, n-butyl group, isobutyl group, s-butyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, and n-eicosanyl group.

Examples of the C1-C20 haloalkyl group include those groups obtained by replacing at least one of the hydrogen atoms of the above C1-C20 alkyl groups with a halogen atom. Among these groups, preferred are fluoroalkyl groups, and more preferred are perfluoroalkyl groups.

Specific examples of them include fluoromethyl group, difluoromethyl group, trifluoromethyl group, pentafluoroethyl group, 2,2,2-trifluoroethyl group, heptafluoropropyl group, 2,2,3,3,3-pentafluoropropyl group, 2,2,3,3-tetrafluoropropyl group, 2,2,2-trifluoro-1-(trifluoromethyl)ethyl group, nonafluorobutyl group, 4,4,4-trifluorobutyl group, undecafluoropentyl group, 2,2,3,3,4,4,5,5,5-nonafluoropentyl group, 2,2,3,3,4,4,5,5-octafluoropentyl group, tridecafluorohexyl group, 2,2,3,3,4,4,5,5,6,6,6-undecafluorohexyl group, 2,2,3,3,4,4,5,5,6,6-decafluorohexyl group, and 3,3,4,4,5,5,6,6,6-nonafluorohexyl group.

Specific examples of the C3-C20 cycloalkyl group include cyclopropyl group, cyclobutyl group, cyclopentyl group, cyclohexyl group, cycloheptyl group, cyclooctyl group, and cyclononyl group.

Specific examples of the C6-C20 bicycloalkyl group include bicyclopropyl group, bicyclobutyl group, bicyclopentyl group, bicyclohexyl group, bicycloheptyl group, bicyclooctyl group, and bicyclononyl group.

Specific examples of the C2-C20 alkenyl group include vinyl group, 1-propenyl group, 2-propenyl group, 1-methyl-2-propenyl group, 2-butenyl group, 3-butenyl group, 2-pentenyl group, 3-pentenyl group, 4-pentenyl group, 2-hexenyl group, 3-hexenyl group, 4-hexenyl group, 5-hexenyl group, 6-heptenyl group, 7-octenyl group, 3,7-dimethyl-6-octenyl group, 8-nonenyl group, 9-decenyl group, 10-undecenyl group, 11-dodecenyl group, 12-tridecenyl group, 13-tetradecenyl group, 14-pentadecenyl group, 15-hexadecenyl group, 16-heptadecenyl group, 17-octadecenyl group, 18-nonadecenyl group, and 19-eicosenyl group.

Specific examples of the C2-C20 alkynyl group include ethynyl group, 1-propynyl group, 2-propynyl group, 1-methyl-2-propynyl group, 2-butynyl group, 3-butynyl group, 2-pentynyl group, 3-pentynyl group, 4-pentynyl group, 2-hexynyl group, 3-hexynyl group, 4-hexynyl group, 5-hexynyl group, 6-heptynyl group, 7-octynyl group, 3,7-dimethyl-6-octynyl group, 8-nonynyl group, 9-decynyl group, 10-undecynyl group, 11-dodecynyl group, 12-tridecynyl group, 13-tetradecynyl group, 14-pentadecynyl group, 15-hexadecynyl group, 16-heptadecynyl group, 17-octadecynyl group, 18-nonadecynyl group, and 19-eicosynyl group.

Specific examples of the C6-C20 aryl group include phenyl group, α-naphthyl group, β-naphthyl group, anthryl group, phenanthrenyl group, o-biphenylyl group, m-biphenylyl group, and p-biphenylyl group.

Specific examples of the C7-C20 aralkyl group include benzyl group, phenylethyl group, phenylpropyl group, naphthylmethyl group, naphthylethyl group, and naphthylpropyl group.

Specific examples of the C1-C20 acyl group include formyl group, acetyl group, propionyl group, butyryl group, isobutyryl group, valeryl group, isovaleryl group, and benzoyl group.

Among these, $R^1$ to $R^4$ are preferably each a hydrogen atom, a halogen atom, a C1-C4 alkyl group, a C1-C4 perfluoroalkyl group, or a C1-C4 alkoxy group, and are optimally all hydrogen atoms, from the viewpoint of enhancing the solubility of the aryldiamine derivative in solvents and enhancing the uniformity of the thin film obtained.

$R^5$ to $R^8$ each independently represent a hydrogen atom, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group, a thienyl group (These groups may be substituted with a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group.), or a group represented by the above formula (2), with at least one of $R^5$ to $R^8$ being a hydrogen atom.

In the above formula (2), $R^9$ to $R^{12}$ each independently represent a hydrogen atom, a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group; and $R^{13}$ and $R^{14}$ each independently represent a phenyl group, a naphthyl group, an anthryl group, a pyridyl group, a pyrimidinyl group, a pyridazinyl group, a pyrazinyl group, a furanyl group, a pyrrolyl group, a pyrazolyl group, an imidazolyl group, a thienyl group (These groups may be bonded to each other to form a ring, and may be substituted with a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group.).

Note that specific examples of the halogen atom, the C1-C20 alkoxy group, C1-C20 thioalkoxy group, C1-C20 alkyl group, C1-C20 haloalkyl group, C3-C20 cycloalkyl group, C6-O20 bicycloalkyl group, C2-C20 alkenyl group, C2-C20 alkynyl group, C6-C20 aryl group, C7-C20 aralkyl group, and C1-C20 acyl group in $R^5$ to $R^{14}$ include the same or similar groups to the above-mentioned.

Among these, $R^5$ and $R^7$ are optimally both hydrogen atoms, and $R^6$ and $R^8$ are optimally both phenyl groups, from the viewpoint of enhancing the solubility of the aryldiamine derivative in solvents and enhancing the uniformity of the thin film obtained.

In the present invention, specific examples of the aryldiamine derivative that can be used preferably include, but are not limited to, the following compounds (formulas (1-1) to (1-4)).

[Chemical Formula 4]

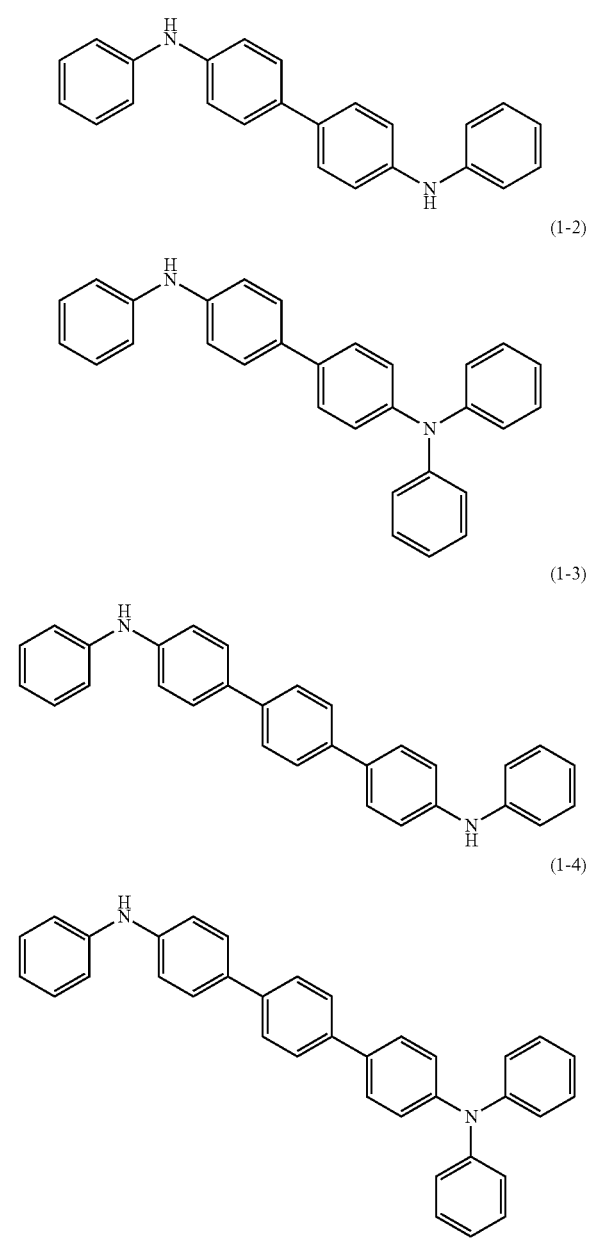

(1-1)

(1-2)

(1-3)

(1-4)

As the aryldiamine derivative represented by the formula (1), a commercialized one may be used, or one produced by a known method using a benzidine, diaminoterfenyl or the like as a starting material may be used. In either case, it is preferable to use an aryldiamine derivative purified by recrystallization or a vapor deposition method, prior to preparation of the composition for an anode buffer layer. By using a purified aryldiamine derivative, it is possible to enhance more the characteristics of an OPV element provided with the thin film obtained from the composition. In the case of purification by recrystallization, for example, 1,4-dioxane, tetrahydrofuran and the like can be used as a solvent.

The molecular weight of the aryldiamine derivative represented by the formula (1) is not particularly limited. Taking conductivity into consideration, the molecular weight is normally at least 200, preferably at least 300, as a lower limit. In consideration of enhancement of solubility in solvents, the molecular weight is up to 5000, preferably up to 2000, as an upper limit.

In the composition for an anode buffer layer of the present invention, as the aryldiamine derivative represented by the formula (1), one compound (in other words, the degree of dispersion of molecular weight distribution is one) selected from the aryldiamine derivatives represented by the formula (1) may be used solely, or two or more compounds selected from the aryldiamine derivatives represented by the formula (1) may be used in combination.

The electron-accepting dopant substance which is another component contained in the composition for an anode buffer layer of the present invention is not specifically restricted, so long as it is soluble in at least one solvent used in the composition for an anode buffer layer.

Specific examples of the electron-accepting dopant substance include: inorganic strong acids such as hydrogen chloride, sulfuric acid, nitric acid, and phosphoric acid; Lewis acids such as aluminum(III) chloride ($AlCl_3$), titanium(IV) tetrachloride ($TiCl_4$), boron tribromide ($BBr_3$), boron trifluoride ether complex ($BF_3 \cdot OEt_2$), iron(III) chloride ($FeCl_3$), copper(II) chloride ($CuCl_2$), antimony(V) pentachloride ($SbCl_5$), arsenic(V) pentafluoride ($AsF_5$), phosphorus pentafluoride ($PF_5$), and tris(4-bromophenyl) aluminum hexachloroantimonate (TBPAH); organic strong acids such as benzenesulfonic acid, tosic acid, camphorsulfonic acid, hydroxybenzenesulfonic acid, 5-sulfosalicylic acid, dodecylbenzenesulfonic acid, polystyrenesulfonic acid, 1,4-benzodioxanedisulfonic acid compounds described in WO 2005/000832, arylsulfonic acid compounds described in WO 2006/025342, and dinonylnaphthalenesulfonic acid compounds described in JP-A 2005-108828; organic oxidants such as 7,7,8,8-tetracyanoquinodimethane (TCNQ), 2,3-dichloro-5,6-dicyano-1,4-benzoquinone (DDQ), and iodine, inorganic oxidants such as heteropolyacids such as phosphomolybdic acid, phosphotungstic acid, and phosphotungstomolybdic acid described in WO 2010/058777. These respective substances may be used in combination.

Among them, preferred are arylsulfonic acid compounds, and particularly preferred are the arylsulfonic acid compounds represented by the formula (3).

[Chemical Formula 5]

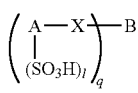

(3)

(In the formula, letter X represents O, letter A represents a naphthalene ring or an anthracene ring, letter B represents a perfluorobiphenyl group having a valence of 2 to 4, letter l represents the number of sulfonic acid groups bonded to the letter A and is an integer satisfying $1 \leq l \leq 4$, letter q represents the number of bonds of the letter B and the letter X and is an integer satisfying 2 to 4.)

In the present invention, specific examples of the arylsulfonic acid compounds which can be used preferably include, but are not limited to, the following compound (formula (3-1)).

[Chemical Formula 6]

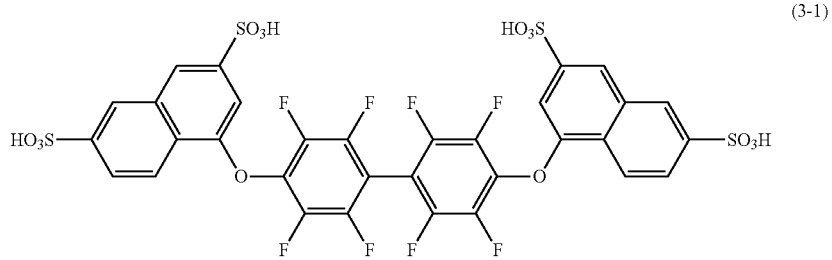

(3-1)

As the organic solvent for use in preparing the composition for an anode buffer layer, high-solvency solvents capable of dissolving the aryldiamine derivative and the electron-accepting dopant substance therein can be used. The high-solvency solvents may be used either singly or as a mixture of two or more of them, and the amount thereof used can be 5% by weight to 100% by weight based on the total weight of the solvent or solvents used in the composition.

Examples of such high-solvency solvents include N-methylformamide, N,N-dimethylformamide, N,N-diethylformamide, N-methylacetamide, N,N-dimethylacetamide, N-methylpyrrolidone, and 1,3-dimethyl-2-imidazolidinone.

Among these, preferred are N-methylformamide, N,N-dimethylformamide, N,N-diethylformamide, N-methylacetamide, and N,N-dimethylacetamide which are amide solvents, and more preferred is N,N-dimethylacetamide.

The charge-transporting substance and the electron-accepting dopant substance are both preferably in the state of being completely dissolved or uniformly dispersed in the above-mentioned organic solvent. From the viewpoint of obtaining, with good reproducibility, a buffer layer giving an organic thin film solar cell having a high conversion efficiency, it is more preferable that these substances are completely dissolved in the above-mentioned organic solvent.

The composition for an anode buffer layer of the present invention preferably contains at least one high-viscosity organic solvent that has a viscosity of 10 mPa·s to 200 mPa·s, particularly 35 mPa·s to 150 mPa·s at 25° C. and has a boiling point of 50° C. to 300° C., particularly 150° C. to 250° C. at normal pressure.

The high-viscosity organic solvent is not specifically restricted, and examples thereof include cyclohexanol, ethylene glycol, 1,3-octylene glycol, diethylene glycol, dipropylene glycol, triethylene glycol, tripropylene glycol, 1,3-butanediol, 2,3-butanediol, 1,4-butanediol, propylene glycol, and hexylene glycol.

The addition ratio of the high-viscosity organic solvent based on the total amount of the solvents used in the composition of the present invention is preferably within such a range that precipitation of solids does not occur. The addition ratio is preferably 5% by weight to 80% by weight, so long as precipitation of solids does not occur.

Further, for purposes such as enhancement of wetting property in regard of a surface to be treated, control of surface tension of solvent, control of polarity, and control of boiling point, other solvent capable of imparting film flatness at the time of a heat treatment can be mixed in a proportion of 1% by weight to 90% by weight, preferably 1% by weight to 50% by weight, based on the total weight of the solvents used in the composition.

Examples of such a solvent include, but are not limited to, butyl cellosolve, diethylene glycol diethyl ether, diethylene glycol dimethyl ether, diethylene glycol monoethyl ether acetate, diethylene glycol monobutyl ether acetate, dipropylene glycol monomethyl ether, propylene glycol monomethyl ether, propylene glycol monomethyl ether acetate, ethyl carbitol, diacetone alcohol, γ-butyrolactone, ethyl lactate, and n-hexyl acetate.

The composition for an anode buffer layer of the present invention desirably contains an organosilane compound, from the viewpoint of enhancing the conversion efficiency of the solar cell obtained.

Examples of the organosilane compound include trialkoxysilanes, dialkoxysilanes, etc., among which preferred are aryltrialkoxysilanes, aryldialkoxysilanes, fluorine atom-containing trialkoxysilanes, and fluorine atom-containing dialkoxysilanes, and more preferred are the silane compounds represented by the formula (S1) or (S2).

[Chemical Formula 7]

RSi(OCH$_3$)$_3$ (S1)

RSi(OC$_2$H$_5$)$_3$ (S2)

(In the formulas, letter R represents a C1-C6 fluoroalkyl group.)

Specific examples of the C1-C6 fluoroalkyl group include trifluoromethyl group, 2,2,2-trifluoroethyl group, 1,1,2,2,2-pentafluoroethyl group, 3,3,3-trifluoropropyl group, 2,2,3,3,3-pentafluoropropyl group, 1,1,2,2,3,3,3-heptafluoropropyl group, 4,4,4-trifluorobutyl group, 3,3,4,4,4-pentafluorobutyl group, 2,2,3,3,4,4,4-heptafluorobutyl group, and 1,1,2,2,3,3,4,4,4-nonafluorobutyl group.

Specific examples of the dialkoxysilane compounds include dimethyldimethoxysilane, dimethyldiethoxysilane, methylethyldimethoxysilane, diethyldimethoxysilane, diethyldiethoxysilane, methylpropyldimethoxysilane, methylpropyldiethoxysilane, diisopropyldimethoxysilane, phenylmethyldimethoxysilane, vinylmethyldimethoxysilane, 3-glycidoxypropylmethyldimethoxysilane, 3-glycidoxypropylmethyldiethoxysilane, 3-(3,4-epoxycyclohexyl)ethylmethyldimethoxysilane, 3-methacryloxypropylmethyldimethoxysilane, 3-methacryloxypropylmethyldiethoxysilane, 3-mercaptopropylmethyldimethoxysilane, γ-aminopropylmethyldiethoxysilane, N-(2-aminoethyl)aminopropylmethyldimethoxysilane, and 3,3,3-trifluoropropylmethyldimethoxysilane.

Specific examples of the trialkoxysilane compounds include methyltrimethoxysilane, methyltriethoxysilane, ethyltrimethoxysilane, ethyltriethoxysilane, propyltrimethoxysilane, propyltriethoxysilane, butyltrimethoxysilane, butyltriethoxysilane, pentyltrimethoxysilane, pentyltriethoxysilane, heptyltrimethoxysilane, heptyltriethoxysilane, octyltrimethoxysilane, octyltriethoxysilane, dodecyltrimethoxysilane, dodecyltriethoxysilane, hexadecyltrimethoxysilane, hexadecyltriethoxysilane, octadecyltrimethoxysilane, octadecyltriethoxysilane, phenyltrimethoxysilane, phenyltriethoxysilane, vinyltrimethoxysilane, vinyltriethoxysilane, γ-aminopropyltrimethoxysilane, 3-aminopropyltriethoxysilane, γ-glycidoxypropyltrimethoxysilane, 3-glycidoxypropyltriethoxysilane, γ-methacryloxypropyltrimethoxysilane, γ-methacryloxypropyltriethoxysilane, triethoxy(4-(trifluoromethyl)phenyl)silane, dodecyltriethoxysilane, 3,3,3-trifluoropropyltrimethoxysilane, (triethoxysilyl)cyclohexane, perfluorooctylethyltriethoxysilane, triethoxyfluorosilane, tridecafluoro-1,1,2,2-tetrahydrooctyltriethoxysilane, 3-(heptafluoroisopropoxy)propyltriethoxysilane, heptadecafluoro-1,1,2,2-tetrahydrodecyltriethoxysilane, triethoxy-2-thienylsilane, and 3-(triethoxysilyl)furan.

In the present invention, the content of the organosilane compound is normally about 0.1% by weight to 200% by weight, preferably 1% by weight to 50% by weight, and more preferably 5% by weight to 20% by weight, based on the charge-transporting substance and the electron-accepting dopant substance in the composition of the present invention.

The concentration of solids in the composition of the present invention is set, as required, taking the viscosity, surface tension and the like of the composition, the thickness of the thin film to be produced, etc. into account. The solids concentration is normally about 0.1% by weight to 10.0% by weight, preferably 0.5% by weight to 5.0% by weight, and more preferably 1.0% by weight to 3.0% by weight.

Note that the solids means other components than the organic solvent that constitute the composition for an anode buffer layer.

In addition, the amount-of-material (mol) ratio between the charge-transporting substance and the electron-accepting dopant substance is set, as required, taking the charge-transporting property to be exhibited, the kinds of the charge-transporting substance and the like into account. The amount-of-material (mol) ratio of the electron-accepting dopant substance to the charge-transporting substance is normally from 0.1 to 10, preferably from 0.5 to 5.0, and more preferably from 0.5 to 3.0.

Besides, the viscosity of the composition for an anode buffer layer used in the present invention is controlled, as required, taking the thickness and the like of the thin film to be produced and the solids concentration into account and according to the coating method. The viscosity is normally about 0.1 mPa·s to 50 mPa·s at 25° C.

In preparing the composition of the present invention, it is possible to mix the charge-transporting substance, the electron-accepting dopant substance, and the organic solvent in an arbitrary order, so long as the solids are uniformly dissolved or dispersed in the solvent. Specifically, for example, a method of dissolving the aryldiamine derivative in the organic solvent and then dissolving the electron-accepting dopant substance in the resulting solution, a method of dissolving the electron-accepting dopant substance in the organic solvent and then dissolving the aryldiamine derivative in the resulting solution, and a method of mixing the aryldiamine derivative and the electron-accepting dopant substance and then putting the mixture into the organic solvent to dissolve the mixture in the organic solvent, can all be adopted, so long as the solids are uniformly dissolved or dispersed in the organic solvent.

In addition, while the preparation of the composition is normally conducted in an inert gas atmosphere at normal temperature and normal pressure, the preparation may be carried out in the atmospheric air (in the presence of oxygen) or with heating, so long as such problems as decomposition of the compounds in the composition or a large change in composition would not occur.

An anode buffer layer of the present invention can be formed by coating an anode of an organic thin film solar cell with the composition for an anode buffer layer described above and baking the composition.

At the time of coating, an optimum method may be adopted from among various wet process methods such as a drop casting method, a spin coating method, a blade coating method, a dip coating method, a roll coating method, a bar coating method, a die coating method, an ink jet method, and a printing method (relief, intaglio, lithography, and screen printing), taking the viscosity and surface tension of the composition, the thickness of the thin film desired, etc. into account.

While the coating is normally conducted in an inert gas atmosphere at normal temperature and normal pressure, the coating may be carried out in the atmospheric air (in the presence of oxygen) or with heating, so long as problems as decomposition of the compounds in the composition or a large change in composition would not occur.

The film thickness is normally preferably about 5 nm to 200 nm. Examples of a method for changing the film thickness include a method in which the concentration of solids in the composition is changed, and a method in which the coating amount at the time of coating is changed.

A method of producing an organic thin film solar cell by use of the composition of the present invention will be described below.

[Formation of Anode Layer]:

Step of Forming Layer of Anode Material on Surface of Transparent Substrate to Produce Transparent Electrode As an anode material, there can be used metal oxides such as indium tin oxide (ITO) and indium zinc oxide (IZO), and highly charge-transporting organic compounds such as polythiophene derivatives and polyaniline derivatives. Besides, as a transparent substrate, there can be used substrates formed from glass or transparent resin.

A method for forming a layer of the anode material (anode layer) is selected, as required, according to the properties of the anode material. Normally, either a dry process (a vapor deposition method) using a sublimable compound or a wet process (particularly, a spin coating method or a slit coating method) using a varnish containing the charge-transporting compound is adopted.

In addition, as the transparent electrode, commercialized ones can also be used preferably. In this case, from the viewpoint of enhancing the yield of the element, it is preferable to use a substrate having been subjected to a smoothing treatment. In the case where a commercialized transparent electrode is used, the method of producing the organic thin film solar cell of the present invention does not include the step of forming the anode layer.

The transparent electrode to be used is preferably washed with a detergent, an alcohol, or pure water before put to use. For example, an anode substrate is preferably subjected to a surface treatment such as a UV ozone treatment, and an oxygen-plasma treatment immediately before put to use (in the case where the anode material has an organic matter as a main constituent, such a surface treatment may be omitted).

[Formation of Anode Buffer Layer]:

Step of Forming Anode Buffer Layer on Layer of Anode Material Formed

According to the above-mentioned method, the buffer layer is formed on the layer of the anode material by use of the composition of the present invention.

[Formation of Active Layer]:

Step of Forming Active Layer on Anode Buffer Layer Formed

An active layer may be a laminate of an n layer which is a thin film composed of an n-type semiconductor material and a p layer which is a thin film composed of a p-type semiconductor material, or may be a non-laminate thin film composed of a mixture of these materials.

Examples of the n-type semiconductor material include fullerenes, [6,6]-phenyl-$C_{61}$-butyric acid methyl ester ($PC_{61}BM$), and [6,6]-phenyl-$C_{71}$-butyric acid methyl ester ($PC_{71}BM$). On the other hand, examples of the p-type semiconductor material include polymers including a thiophene skeleton in a main chain thereof such as regioregular poly(3-hexylthiophene) (P3HT), PTB7 (formula (4)), PDTP-DFBT (formula (5)), and thienothiophene unit-containing polymers described in JP-A 2009-158921 and WO 2010/008672, phthalocyanines such as CuPC and ZnPC, and porphyrins such as tetrabenzoporphyrin.

Among these, $PC_{61}BM$ and $PC_{71}BM$ are preferable as the n-type material, whereas the polymers including a thiophene skeleton in a main chain thereof such as PTB7 are preferable as the p-type material.

Note that "a thiophene skeleton in a main chain" represents a divalent aromatic ring consisting only of thiophene or a divalent condensed aromatic ring including at least one thiophene, such as thienothiophene, benzothiophene, dibenzothiophene, benzodithiophene, naphthothiophene, naphtodithiophene, anthrathiophene, and anthradithiophene, and these may be substituted with a substituent group represented by the above-mentioned $R^1$ to $R^8$.

A method for forming the active layer is selected, as required, according to the properties of the n-type semiconductor material or p-type semiconductor material. Normally, either a dry process (particularly, a vapor deposition method) using a sublimable compound or a wet process (particularly, a spin coating method or a slit coating method) using a varnish containing the material is adopted.

[Chemical Formula 8]

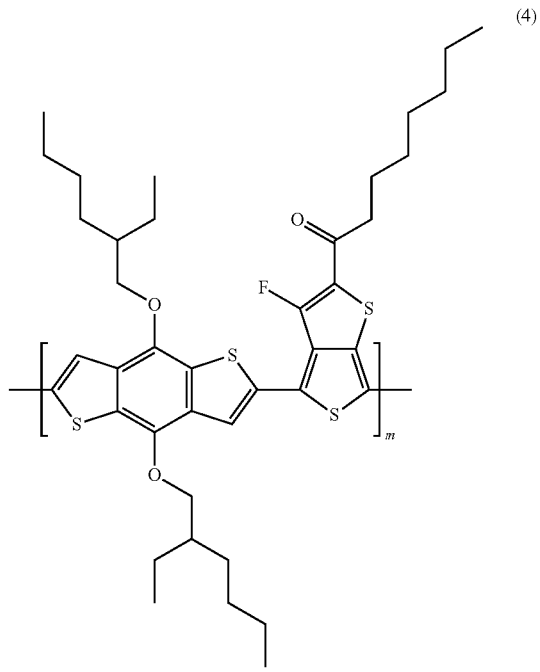

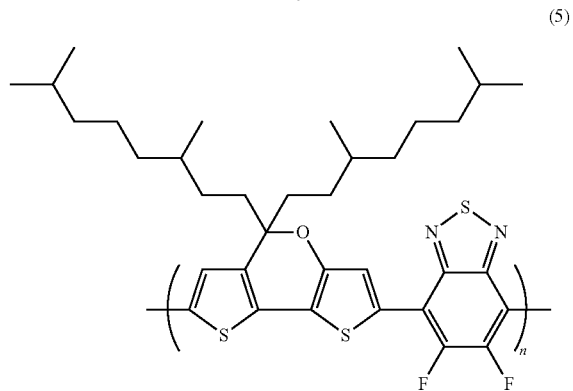

(In the formulas, letter m and letter n each indicate the number of recurring units and represent a positive integer.)

[Formation of Cathode Buffer Layer]:

Step of Forming Cathode Buffer Layer on Active Layer Formed

If necessary, a cathode buffer layer may be formed between the active layer and a cathode layer, for such purposes as achieving a higher charge movement efficiency.

Examples of a material for forming the cathode buffer layer include lithium oxide ($Li_2O$), magnesium oxide (MgO), alumina ($Al_2O_3$), lithium fluoride (LiF), magnesium fluoride ($MgF_2$), and strontium fluoride ($SrF_2$).

A method for forming the cathode buffer layer is selected, as required, according to the properties of the material. Normally, either a dry process (particularly, a vapor deposition method) using a sublimable compound or a wet process (particularly, a spin coating method or a slit coating method) using a varnish containing the material is adopted.

[Formation of Cathode Layer]:

Step of Forming Cathode Layer on Cathode Buffer Layer Formed

Examples of a cathode material include aluminum, magnesium-silver alloy, aluminum-lithium alloy, lithium, sodium, potassium, cesium, calcium, barium, silver, and gold. A plurality of cathode materials can be used in a laminated state or a mixed state.

The method for forming the cathode buffer layer is selected, as required, according to the properties of the material. Normally, a dry process (particularly, a vapor deposition method) is adopted.

[Formation of Carrier Block Layer]

When necessary, a carrier block layer may be provided between arbitrary layers, for such purposes as controlling rectification properties of a photocurrent.

Examples of a material for forming the carrier block layer include titanium oxide, and zinc oxide.

A method for forming the carrier block layer is selected, as required, according to the properties of the material. Normally, where a sublimable compound is used, a vapor deposition method is adopted. Where a varnish in which the material is dissolved is used, either a spin coating method or a slit coating method is adopted.

The OPV element produced by the above-exemplified method may be again introduced into a glove box and is subjected to a sealing operation in an atmosphere of an inert gas such as nitrogen, for preventing the element from being deteriorated due to the atmospheric air. The OPV element in the sealed state can be made to exhibit the function as a solar cell, or can be put to measurement of solar cell characteristics.

Examples of the sealing method include a method in which a recessed-type glass substrate with a UV-curable resin adhered to an end portion is adhered to a film formation surface side of the organic thin film solar cell element in an inert gas atmosphere, and the resin is cured by irradiation with UV rays, and a method in which film sealing type sealing is conducted by such a technique as sputtering in vacuum.

EXAMPLES

The present invention will be described more specifically below by showing Examples and Comparative Examples, but the present invention is not to be restricted to the following Examples.

[1] Apparatuses Used (1) NMR
Apparatus: ECX-300, manufactured by JEOL Ltd.
Solvent for measurement: dimethyl sulfoxide-d6, manufactured by Junsei Chemical Co., Ltd.
(2) Glove box: VAC Glove Box System, manufactured by Yamahachi & Co., Ltd.
(3) Vapor deposition apparatus: Vacuum Vapor Deposition Apparatus, manufactured by Aoyama Engineering K.K.
(4) Solar simulator: OTENTOSUN-III, manufactured by Bunkoukeiki K.K.; AM 1.5 G filter, radiation intensity: 100 mW/cm$^2$
(5) Source measure unit: 2612A, manufactured by Keithley Instruments K.K.

[2] Preparation of Composition for Active Layer

Preparation Example 1

Into a sample bottle containing 40 mg of regioregular poly(3-hexylthiophene) (product name: lisicon (registered trademark) SP-001, manufactured by Merck) and 32 mg of PC$_{61}$BM (product name: nanom spectra E100, manufactured by Frontier Carbon Corporation), was added 2.0 mL of chlorobenzene, followed by stirring on a hot plate at 80° C. for 15 hours, to obtain solution A1 (composition for active layer).

Preparation Example 2

Into a sample bottle containing 20 mg of PTB7 (manufactured by 1-Material) and 30 mg of PC$_{61}$BM (product name: nanom spectra E100, manufactured by Frontier Carbon Corporation), was added 2.0 mL of chlorobenzene, followed by stirring on a hot plate at 80° C. for 15 hours. After this solution was let cool to room temperature, 60 μL of 1,8-diiodooctane (manufactured by Tokyo Chemical Industry Co., Ltd.) was added thereto, followed by stirring, to obtain solution A2 (composition for active layer).

Preparation Example 3

Into a sample bottle containing 20 mg of PDTP-DFBT (manufactured by 1-Material) and 30 mg of PC$_{61}$BM (product name: nanom spectra E100, manufactured by Frontier Carbon Corporation), was added 2.0 mL of chlorobenzene, followed by stirring on a hot plate at 80° C. for 15 hours. After this solution was let cool to room temperature, 60 μL of 1,8-diiodooctane (manufactured by Tokyo Chemical Industry Co., Ltd.) was added thereto, followed by stirring, to obtain solution A3 (composition for active layer).

[3] Preparation of Composition for Anode Buffer Layer of OPV

Preparation Example 4

To a mixture of 132.1 mg (0.393 mmol) of N,N'-diphenylbenzidine (manufactured by Tokyo Chemical Industry Co., Ltd., the same applies hereinafter) and 177.2 mg (0.196 mmol) of an arylsulfonic acid compound represented by the above formula (3-1) synthesized according to the method described in WO 2006/025342, was added 5.0 g of N,N-dimethylacetamide, followed by stirring at room temperature with irradiation with ultrasonic waves, to effect dissolution. Further, 5.0 g of cyclohexanol was added to the resulting solution, followed by stirring, to obtain a light yellow solution. The light yellow solution obtained was filtered through a syringe filter having a pore diameter of 0.2 μm, to obtain a composition for anode buffer layer B1.

Preparation Example 5

To 10.0 g of N,N-dimethylacetamide were added 0.717 mg (3.61 mmol) of phenyltrimethoxysilane (manufactured by Shin-Etsu Chemical Co., Ltd.) and 0.394 mg (1.81 mmol) of 3,3,3-trifluoropropyltrimethoxysilane (manufactured by Shin-Etsu Chemical Co., Ltd.), followed by stirring at room temperature, to obtain a silane compound solution S1.

Preparation Example 6

To 10.0 g of 1,3-dimethyl-2-imidazolidinone were added 0.717 mg (3.61 mmol) of phenyltrimethoxysilane (manufactured by Shin-Etsu Chemical Co., Ltd.) and 0.394 mg (1.81 mmol) of 3,3,3-trifluoropropyltrimethoxysilane (manufactured by Shin-Etsu Chemical Co., Ltd.), followed by stirring at room temperature, to obtain a silane compound solution S2.

Preparation Example 7

To a mixture of 92.5 mg (0.275 mmol) of N,N'-diphenylbenzidine and 186.1 mg (0.206 mmol) of an arylsulfonic acid compound represented by the above formula (3-1) synthesized according to the method described in WO 2006/025342, was added 4.72 g of N,N-dimethylacetamide, followed by stirring at room temperature with irradiation with ultrasonic waves to effect dissolution. Further, 5.0 g of cyclohexanol was added to the resulting solution, followed by stirring, and then 0.31 g of the silane compound solution S1 was added thereto, to obtain a light yellow solution.

The light yellow solution obtained was filtered through a syringe filter having a pore diameter of 0.2 μm, to obtain a composition for anode buffer layer B2.

Preparation Example 8

To a mixture of 61.0 mg (0.181 mmol) of N,N'-diphenylbenzidine and 122.8 mg (0.136 mmol) of an arylsulfonic acid compound represented by the above formula (3-1) synthesized according to the method described in WO 2006/025342, was added 4.82 g of N,N-dimethylacetamide, followed by stirring at room temperature with irradiation with ultrasonic waves to effect dissolution. Further, 5.0 g of cyclohexanol was added to the resulting solution, followed by stirring, and then 0.21 g of the silane compound solution S1 was added thereto, to obtain a light yellow solution.

The light yellow solution obtained was filtered through a syringe filter having a pore diameter of 0.2 μm, to obtain a composition for anode buffer layer B3.

Preparation Example 9

To a mixture of 61.0 mg (0.181 mmol) of N,N'-diphenylbenzidine and 122.8 mg (0.136 mmol) of an arylsulfonic acid compound represented by the above formula (3-1) synthesized according to the method described in WO 2006/025342, were added 3.15 g of N,N-dimethylacetamide and 1.67 g of 2,3-butanediol, followed by stirring at room temperature with irradiation with ultrasonic waves to effect dissolution. Further, 5.0 g of cyclohexanol was added to the resulting solution, followed by stirring, and then 0.21 g of the silane compound solution S1 was added thereto, to obtain a light brown solution.

The light brown solution obtained was filtered through a syringe filter having a pore diameter of 0.2 Inn, to obtain a composition for anode buffer layer B4.

Preparation Example 10

To a mixture of 61.0 mg (0.181 mmol) of N,N'-diphenylbenzidine and 122.8 mg (0.136 mmol) of an arylsulfonic acid compound represented by the above formula (3-1) synthesized according to the method described in WO 2006/025342, were added 3.15 g of 1,3-dimethyl-2-imidazolidinone and 1.67 g of propylene glycol, followed by stirring at room temperature with irradiation with ultrasonic waves to effect dissolution. Further, 5.0 g of cyclohexanol was added to the resulting solution, followed by stirring, and then 0.21 g of the silane compound solution S2 was added thereto, to obtain a light brown solution.

The light brown solution obtained was filtered through a syringe filter having a pore diameter of 0.2 μm, to obtain a composition for anode buffer layer B5.

Comparative Preparation Example 1

PEDOT/PSS (Clevios P VP CH8000, manufactured by Heraeus) was filtered through a syringe filter having a pore diameter of 0.45 μm, to obtain a composition for anode buffer layer C1.

[4] Fabrication of Organic Thin Film Solar Cell

Example 1

A glass substrate measuring 20 mm by 20 mm on which an ITO transparent conductor layer to be positive electrode was patterned in a 2 mm by 20 mm stripe pattern was subjected to a UV/ozone treatment for 15 minutes, and was coated with the composition for anode buffer layer B1 by a spin coating method. The glass substrate was heated by use of a hot plate at 50° C. for five minutes and further at 230° C. for 20 minutes, to form a buffer layer having a thickness of 30 nm.

Thereafter, in a glove box flushed with an inert gas, the solution A1 was dripped onto the buffer layer formed, a film was formed by a spin coating method, and heating was conducted using a hot plate at 80° C. for 30 minutes, to form an active layer having a thickness of 90 nm.

Next, the substrate formed with the organic semiconductor layer and a mask for cathode were placed in a vacuum vapor deposition apparatus, the apparatus was evacuated to a vacuum degree of up to $1\times10^{-3}$ Pa, and an aluminum layer to be a negative electrode was vapor deposited in a thickness of 80 nm by a resistance heating method.

Finally, heating was conducted using a hot plate at 135° C. for 10 minutes, to fabricate an OPV element wherein the area of intersection of the stripe-patterned ITO layer and the aluminum layer was 2 mm by 2 mm.

Example 2

An OPV element was fabricated by the same method as in Example 1, except that the composition for anode buffer layer B2 was used in place of the composition for anode buffer layer B1.

Example 3

A glass substrate measuring 20 mm by 20 mm on which an ITO transparent conductor layer to be a positive electrode was patterned in a 2 mm by 20 mm stripe pattern was subjected to a UV/ozone treatment for 15 minutes, and was then coated with the composition for anode buffer layer B1 prepared on the substrate by a spin coating method. This glass substrate was heated by use of a hot plate at 50° C. for five minutes and further at 230° C. for 20 minutes, to form a buffer layer having a thickness of 30 nm.

Thereafter, in a glove box flushed with an inert gas, the solution A2 was dripped onto the buffer layer formed, and a film was formed by a spin coating method.

Next, the substrate formed with the organic semiconductor layer and a mask for cathode were placed in a vacuum vapor deposition apparatus, the apparatus was evacuated to a vacuum degree of up to $1\times10^{-3}$ Pa, and an aluminum layer to be a negative electrode was vapor deposited in a thickness of 80 nm by a resistance heating method.

Finally, heating was conducted using a hot plate at 90° C. for 10 minutes, to fabricate an OPV element wherein the area of intersection of the striped ITO layer and the aluminum layer was 2 mm by 2 mm.

Example 4

An OPV element was fabricated by the same method as in Example 3, except that the composition for anode buffer layer B2 was used in place of the composition for anode buffer layer B1.

Example 5

An OPV element was fabricated by the same method as in Example 3, except that the composition for active layer A3 was used in place of the composition for active layer A2.

Example 6

An OPV element was fabricated by the same method as in Example 3, except that the composition for active layer A3 was used in place of the composition for active layer A2 and that the composition for anode buffer layer B3 was used in place of the composition for anode buffer layer B1.

Example 7

An OPV element was fabricated by the same method as in Example 3, except that the composition for anode buffer layer B3 was used in place of the composition for anode buffer layer B1.

Example 8

An OPV element was fabricated by the same method as in Example 3, except that the composition for anode buffer layer B4 was used in place of the composition for anode buffer layer B1.

Example 9

An OPV element was fabricated by the same method as in Example 3, except that the composition for anode buffer layer B5 was used in place of the composition for anode buffer layer B1.

Comparative Example 1

An OPV element was fabricated by the same method as in Example 1, except that the composition for anode buffer layer C1 was used in place of the composition for anode buffer layer B1 and that heating at 150° C. for 20 minutes was performed in place of the heating at 230° C. for 20 minutes.

Comparative Example 2

An OPV element was fabricated by the same method as in Example 3, except that the composition for anode buffer layer C1 was used in place of the composition for anode buffer layer B1 and that heating at 150° C. for 20 minutes was performed in place of the heating at 230° C. for 20 minutes.

Comparative Example 3

An OPV element was fabricated by the same method as in Example 3, except that the composition for active layer A3 was used in place of the composition for active layer A2, the composition for anode buffer layer C1 was used in place of the composition for anode buffer layer B1, and heating at 150° C. for 20 minutes was conducted in place of the heating at 230° C. for 20 minutes.

[5] Evaluation of Characteristics

The OPV elements fabricated were put to evaluation of short-circuit current density ($J_{sc}$ [mA/cm$^2$]), open-circuit voltage ($V_{oc}$ [V]), fill factor (FF), and photoelectric conversion efficiency (PCE [%]). The evaluation results in the case where the solution A1 was used as the composition for active layer (Examples 1 and 2 and Comparative Example 1) are set forth in Table 1, the evaluation results in the case where the solution A2 was used (Examples 3 and 4 and Comparative Example 2) are set forth in Table 2, and the evaluation results in the case where the solution A3 was used (Examples 5 and 6 and Comparative Example 3) are set forth in Table 3. In addition, the evaluation results in the case where the composition of the composition for anode buffer layer was changed (Examples 4, 7, 8, and 9) are set forth in Table 4.

Note that the photoelectric conversion efficiency was calculated by the formula of:

$$(\text{photoelectric conversion efficiency}) = (\text{short} - \text{circuit current density}) \times (\text{open} - \text{circuit voltage}) \times (\text{fill factor})/(\text{incident light intensity}).$$

TABLE 1

| | $J_{sc}$ | $V_{oc}$ | FF | PCE |
|---|---|---|---|---|
| Example 1 | 8.3 | 0.56 | 0.58 | 2.7 |
| Example 2 | 8.5 | 0.57 | 0.58 | 2.8 |
| Comparative Example 1 | 8.9 | 0.61 | 0.43 | 2.3 |

TABLE 2

| | $J_{sc}$ | $V_{oc}$ | FF | PCE |
|---|---|---|---|---|
| Example 3 | 13.2 | 0.77 | 0.58 | 5.9 |
| Example 4 | 13.4 | 0.78 | 0.61 | 6.4 |
| Comparative Example 2 | 12.8 | 0.79 | 0.29 | 2.9 |

TABLE 3

| | $J_{sc}$ | $V_{oc}$ | FF | PCE |
|---|---|---|---|---|
| Example 5 | 9.6 | 0.72 | 0.36 | 2.5 |
| Example 6 | 10.1 | 0.74 | 0.37 | 2.8 |
| Comparative Example 3 | 4.2 | 0.75 | 0.17 | 0.5 |

TABLE 4

| | $J_{sc}$ | $V_{oc}$ | FF | PCE |
|---|---|---|---|---|
| Example 4 | 12.5 | 0.76 | 0.49 | 4.6 |
| Example 7 | 12.6 | 0.76 | 0.57 | 5.5 |
| Example 8 | 12.6 | 0.75 | 0.57 | 5.5 |
| Example 9 | 12.7 | 0.73 | 0.54 | 5.0 |

As shown in Tables 1 to 4, the OPV elements provided with the thin film obtained from the composition for anode buffer layer of the present invention as the anode buffer layer showed high photoelectric conversion efficiencies (PCE) as compared to the OPV elements provided with the thin film obtained from PEDOT/PSS in general use as the anode buffer layer, independently of the kind of the composition for active layer.

Thus, it is seen that by use of the composition for anode buffer layer of the present invention, OPV elements with excellent photoelectric conversion characteristics can be produced.

The invention claimed is:

1. An organic thin film solar cell comprising:
an anode buffer layer produced from a composition for an anode buffer layer of an organic thin film solar cell; and
an active layer provided in such a manner as to make contact with the anode buffer layer;
wherein the composition comprises:
a charge-transporting substance including an aryldiamine derivative represented by the formula (1);
an electron-accepting dopant substance;
an organosilane compound; and
an organic solvent

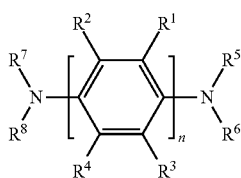
(1)

wherein
$R^1$ to $R^4$ each independently represent a hydrogen atom, a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group,
$R^5$ to $R^8$ each independently represent a hydrogen atom, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group, a thienyl group wherein these groups may be substituted with a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group, or a group represented by the formula (2) provided that at least one of $R^5$ to $R^8$ is a hydrogen atom,

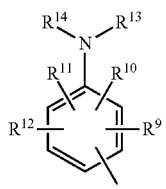
(2)

wherein
$R^9$ to $R^{12}$ each independently represent a hydrogen atom, a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group, and
$R^{13}$ and $R^{14}$ each independently represent a phenyl group, a naphthyl group, an anthryl group, a pyridyl group, a pyrimidinyl group, a pyridazinyl group, a pyrazinyl group, a furanyl group, a pyrrolyl group, a pyrazolyl group, an imidazolyl group, a thienyl group wherein these groups may be bonded to each other to form a ring, and may be substituted with a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group, and
n represents an integer of 2 to 5.

2. The organic thin film solar cell according to claim 1, wherein $R^5$ and $R^7$ are hydrogen atoms, and $R^6$ and $R^8$ are phenyl groups.

3. The organic thin film solar cell according to claim 1 or 2, wherein n is 2 or 3.

4. The organic thin film solar cell according to claim 1, wherein the electron-accepting dopant substance includes an arylsulfonic acid compound.

5. The organic thin film solar cell according to claim 4, wherein the arylsulfonic acid compound is represented by the formula (3),

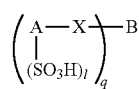
(3)

wherein letter X represents O, letter A represents a naphthalene ring or an anthracene ring, letter B represents a perfluorobiphenyl group having a valence of 2 to 4, letter l represents the number of sulfonic acid groups bonded to the letter A and is an integer satisfying $1 \leq l \leq 4$, and letter q represents the number of bonds of the letter B and the letter X and is an integer satisfying 2 to 4.

6. The organic thin film solar cell according to claim 5, wherein the letter X represents O, and the letter A represents a naphthalene ring or an anthracene ring.

7. The organic thin film solar cell according to claim 1, wherein the active layer includes a fullerene derivative.

8. The organic thin film solar cell according to claim 1, wherein the active layer includes a polymer including a thiophene skeleton in a main chain.

9. The organic thin film solar cell according to claim 1, wherein the active layer includes a fullerene derivative and a polymer including a thiophene skeleton in a main chain.

10. An organic thin film solar cell comprising:
an anode buffer layer produced from a composition, for an anode buffer layer of an organic thin film solar cell, comprising: a charge-transporting substance including an aryldiamine derivative represented by the formula (1); an electron-accepting dopant substance; and an organic solvent

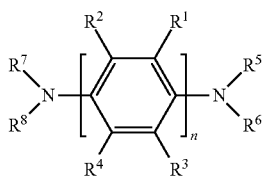

(1)

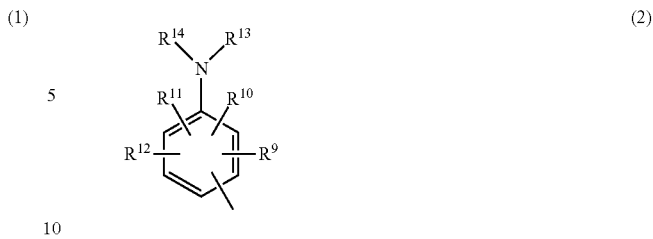

(2)

wherein
n represents an integer of 2 to 5,
$R^1$ to $R^4$ each independently represent a hydrogen atom, a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group, $R^5$ to $R^8$ each independently represent a hydrogen atom, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group, a thienyl group wherein these groups may be substituted with a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group, or a group represented by the formula (2) provided that at least one of $R^5$ to $R^8$ is a hydrogen atom, wherein
$R^9$ to $R^{12}$ each independently represent a hydrogen atom, a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group, and $R^{13}$ and $R^{14}$ each independently represent a phenyl group, a naphthyl group, an anthryl group, a pyridyl group, a pyrimidinyl group, a pyridazinyl group, a pyrazinyl group, a furanyl group, a pyrrolyl group, a pyrazolyl group, an imidazolyl group, a thienyl group wherein these groups may be bonded to each other to form a ring, and may be substituted with a halogen atom, a nitro group, a cyano group, a hydroxyl group, a thiol group, a phosphoric acid group, a sulfonic acid group, a carboxyl group, a C1-C20 alkoxy group, a C1-C20 thioalkoxy group, a C1-C20 alkyl group, a C1-C20 haloalkyl group, a C3-C20 cycloalkyl group, a C6-C20 bicycloalkyl group, a C2-C20 alkenyl group, a C2-C20 alkynyl group, a C6-C20 aryl group, a C7-C20 aralkyl group, or a C1-C20 acyl group; and an active layer provided in such a manner as to make contact with the anode buffer layer.

* * * * *